(12) United States Patent
Or

(10) Patent No.: US 10,815,449 B2
(45) Date of Patent: Oct. 27, 2020

(54) COMPOSITIONS FOR REDUCING ACIDITY

(71) Applicant: MILLSTONEOILS LTD., Kibbutz Yifat (IL)

(72) Inventor: Pinhas Or, Ahuzat Barak (IL)

(73) Assignee: Pinhas Or, Kibbutz Yifat (IL)

( * ) Notice: Subject to any disclaimer, the term of this patent is extended or adjusted under 35 U.S.C. 154(b) by 61 days.

(21) Appl. No.: 15/514,521

(22) PCT Filed: Oct. 1, 2015

(86) PCT No.: PCT/IL2015/050986
§ 371 (c)(1),
(2) Date: Mar. 26, 2017

(87) PCT Pub. No.: WO2016/051412
PCT Pub. Date: Apr. 7, 2016

(65) Prior Publication Data
US 2017/0226444 A1    Aug. 10, 2017

Related U.S. Application Data

(60) Provisional application No. 62/058,726, filed on Oct. 2, 2014.

(51) Int. Cl.
| | | |
|---|---|---|
| C11B 3/10 | (2006.01) | |
| A23D 9/007 | (2006.01) | |
| A23L 33/00 | (2016.01) | |
| A61K 33/06 | (2006.01) | |
| A61K 36/899 | (2006.01) | |
| A61K 33/00 | (2006.01) | |
| A61K 33/08 | (2006.01) | |
| A61K 33/26 | (2006.01) | |
| A23D 9/013 | (2006.01) | |
| C11B 1/06 | (2006.01) | |
| C11B 3/00 | (2006.01) | |
| C11B 3/14 | (2006.01) | |
| A61P 1/04 | (2006.01) | |
| A61K 33/24 | (2019.01) | |
| A61K 33/32 | (2006.01) | |
| A23L 33/16 | (2016.01) | |

(52) U.S. Cl.
CPC ............... *C11B 3/10* (2013.01); *A23D 9/007* (2013.01); *A23D 9/013* (2013.01); *A23L 33/16* (2016.08); *A23L 33/30* (2016.08); *A61K 33/00* (2013.01); *A61K 33/06* (2013.01); *A61K 33/08* (2013.01); *A61K 33/24* (2013.01); *A61K 33/26* (2013.01); *A61K 33/32* (2013.01); *A61K 36/899* (2013.01); *A61P 1/04* (2018.01); *C11B 1/06* (2013.01); *C11B 3/001* (2013.01); *C11B 3/008* (2013.01); *C11B 3/14* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 3,522,145 A | 7/1970 | Apostolatos | |
| 3,678,084 A | 7/1972 | Renold | |
| 4,443,379 A | 4/1984 | Taylor | |
| 2007/0154603 A1 | 7/2007 | Witham | |
| 2009/0140830 A1* | 6/2009 | Amanullah | H01B 3/20 336/94 |
| 2010/0147771 A1 | 6/2010 | McNeff et al. | |

FOREIGN PATENT DOCUMENTS

| | | | |
|---|---|---|---|
| CN | 101831352 A | 9/2010 | |
| EP | 1120379 A1 | 8/2001 | |
| GB | 1190095 A | 4/1970 | |
| GB | 2076008 A | 11/1981 | |
| JP | S5965016 A | 4/1984 | |
| JP | 2013082607 A | 5/2013 | |
| RU | 2392299 C2 * | 6/2010 | |
| RU | 2392299 C2 | 6/2010 | |
| WO | WO-93/23142 A1 | 11/1993 | |

OTHER PUBLICATIONS

English language translation of RU 2392299 C2. (Year: 2010).*
Thomas E. Furia: CRC Handbook of food additives. CRC Press, Jan. 1, 1973, pp. 384-385.
International Search Report of PCT/IL2015/050986 Completed: Jan. 20, 2016; dated Jan. 20, 2016, 4 pages.
Written Opinion of PCT/IL2015/050986 completed: Jan. 20, 2016; dated Jan. 20, 2016 7 pages.

* cited by examiner

*Primary Examiner* — Dominic Lazaro
(74) *Attorney, Agent, or Firm* — Mark S. Cohen; Pearl Cohen Zedek Latzer Baratz LLP

(57) ABSTRACT

The present invention provides a composition based on a starch powder (such as flour), wheat germ, $SiO_2$, MgO, $Al_2O_3$, $Fe_2O_3$, and $K_2O$. This composition is extremely useful in treating acid related disorders and reducing the acidity, removing water, deodorizing, from plant oil and extending the oils shelf life of 3-5 years instead of the average one-year available.

2 Claims, No Drawings

COMPOSITIONS FOR REDUCING ACIDITY

FIELD OF INVENTION

This invention is directed to; inter alia, compositions comprising: a starch powder (such as flour), $SiO_2$, MgO, $Al_2O_3$, $Fe_2O_3$, and $K_2O$ for enhancing the quality of edible oils or rendering non-edible oils-edible.

BACKGROUND OF THE INVENTION

Oil is an essential component of human nutrition, and is one of the basic food groups. It is a staple item in every kitchen, known to be beneficial to the body and to contribute to proper development.

The uniqueness and benefits of olive oil are predominantly attributed to oleic acid—a mono-unsaturated fatty acid of the Cis configurationally isomer. Olive oil is resistant to oxidation and its presence in blood lipid structures inhibits the development of atherosclerotic processes, thought to be the primary cause of heart attacks. For example, in Greece, where only extra virgin olive oil is consumed and refined oil is avoided, the rate of coronary heart disease is exceptionally low. Conversely, in the United States—notorious for consumption of hydrogenated oils—cardiovascular diseases are the nation's number one cause of mortality.

Olive oil is very rich in anti-oxidants, which trap free radicals, thereby inhibiting development of a wide range of pathological processes. Moreover, olive oil is considered to be a source of energy available to the body.

Globally, a large percentage of the olive oil produced is of low quality, with high levels of acidity. This is caused by exposure to unfavorable conditions at the time of growth, production, or storage. The size of the global olive oil market is expected to reach 3.88 million tons by the end of 2012. Sixty percent of total production is low quality oils. Out of the total production of low quality oils, 20% of production is virgin olive oil with-1% to 2% acidity, 20% of production is ordinary virgin olive oil with 2%-3.3% acidity and 20% of production is olive oil, the highest in acidity is about 3.3% The main factors leading to impaired oil quality and increased acidity are hydrolysis and processes of oxidation. Hydrolysis is a process that begins to occur when the oil is still inside the fruit—causes the decomposition of triglyceride molecules and the release of fatty acids, the result of which causes an increase in acidity. Oxidation is a process that takes place subsequent to production, due to exposure to unfavorable conditions. The result of oxidation is undesirable chemical changes in the texture of the olive oil.

Olive oil classifications according to quality are: Extra Virgin: The highest quality oil, with free fatty acids levels no higher than 0.8%. Virgin olive oil: distinguished from "extra virgin" by the fact that free fatty acids levels may reach up to 2.0%. Ordinary virgin olive oil: contains up to 3.3% free fatty acids. This oil does not require special indication.

Olive Oil: Contains over 3.3% free fatty acids. This oil is designated for refining, or for the cosmetic industry, soap, etc. This oil comprises 20% of the global olive oil market. The reasons for this stem from growth conditions and late harvests, which lead the crops to fall to the ground. Humidity and contact with the ground accelerate microbial deterioration and lead to increased rates of acidity.

Olive oil is a product that is sensitive to hostile conditions, and especially to heat and oxygen. Exposure to high temperatures in the presence of oxygen leads to oxidation of the oil and to a range of other chemical and physical changes. During the deterioration process, free-radicals are generated and molecules assume a new identity—one which may be poisonous to the body. In addition, refinement may also change the spatial arrangement of the molecules and may turn the essential CIS oleic acid into trans-oleic acid. Trans-fatty acids may crystallize, creating a physical structure with the potential to settle in blood vessels and accelerate harmful Atherosclerotic processes.

Additionally, during the refining process there are solvents used, which are harmful to the body, and therefore regular consumption of olive oil may put the consumer at risk of poisoning and of developing various pathological processes in the long run.

In general, it is important to note that every substance has the potential to endure changes resulting from interactions, either internally with its own components, or externally with its environment. The occurrence and rate of such interactions depend on environmental conditions, as temperature is known to be a physical parameter that stimulates and accelerates any interaction. Hence, storing oil at low temperatures (room temperature) and avoiding exposure to heat can almost entirely preclude the occurrence of such interactions, thus preserving the substance in its pure state without incurring any adverse changes.

SUMMARY OF THE INVENTION

In one embodiment, provided herein a composition comprising: flour, $SiO_2$ MgO, $Al_2O_3$, $Fe_2O_3$, and $K_2O$.

In one embodiment, provided herein a composition comprising: flour, clay, wheat-germ, and silicate.

In another embodiment, composition of the invention further comprises: $3MgO.4SiO_2.H_2O$, $TiO_2$, MnO, $P_2O$, or any combination thereof. In another embodiment, composition of the invention further comprises: oil, fruit, vegetable, or any combination thereof. In another embodiment, composition of the invention further comprises a monoglyceride. In another embodiment, composition of the invention formulated as an oral or a topical dosage form.

In one embodiment, provided herein a method for treating a subject afflicted with: ulcer, heartburn, gastro-esophageal reflux disease, a gastrointestinal cyst, an acid reflux disease, or any combination thereof, comprising administering to the subject a composition comprising: (a) flour; (b) silicate, $SiO_2$, or their combination; and (c) MgO, $Al_2O_3$, $Fe_2O_3$, $K_2O$, clay, wheat-germ or any combination thereof, thereby treating a subject afflicted with: ulcer, heartburn, gastro-esophageal reflux disease, a gastrointestinal cyst, an acid reflux disease, or any combination thereof.

In one embodiment, provided herein a method for reducing the acidity, removing water, deodorizing, removing peroxides, or any combination thereof from plant oil, comprising the step of mixing a composition as described herein in a plant oil, thereby reducing the acidity, removing water, deodorizing, removing peroxides, or any combination thereof from plant oil.

DETAILED DESCRIPTION OF THE INVENTION

In one embodiment, the present invention provides a novel edible composition to be used in a physical process, which occurs at room temperature for removing free fatty acids from oil. In another embodiment, the composition of the invention and the process utilizing it does not cause any adverse changes to the chemical make-up of oil. In another embodiment, the composition of the invention and the process utilizing it is free of any organic solvents. In another embodiment, the composition of the invention is a mixture of edible that are environmentally friendly, and have been approved as nutritional supplements with no potential risk of bodily harm. In another embodiment, the composition of the invention is a mixture of substances known to promote digestion. In another embodiment, the composition of the invention quickly separates from the oil. In another embodiment, the process and the composition of the invention for removing free fatty acids from oil do not involve an oxidation process. In another embodiment, the process and the composition of the invention for removing free fatty acids from oil do not generate free radicals.

In one embodiment, the present invention provided a composition and method for reducing and maintaining the acidity of a liquid composition. In one embodiment, the present invention provides a composition and method for reducing and maintaining the acidity of a target composition. In one embodiment, the present invention provides that the target composition is a fluidic and/or liquid composition. In one embodiment a target composition as described herein is oily. In one embodiment a target composition as described herein is hydrophobic. In one embodiment, the present invention provides that the target composition is a dry composition. In one embodiment, the present invention provides that the target composition is a nutraceutical and/or pharmaceutical composition. In one embodiment, the present invention provides a method for reducing and/or maintaining the acidity of a target composition. In one embodiment, the present invention provides a method and a composition for prolonging the shelf-life of a target composition. In one embodiment, the present invention provides a method and a composition for inhibiting and/or reducing hydrolysis of a target composition.

In one embodiment, the present invention provides a method and a composition for maintaining the acidity level of a target composition within the range of +/−5% to +/−25%. In one embodiment, the present invention provides a method and a composition for maintaining the acidity level of a target composition within the range of +/−10% to +/−20%. In one embodiment, the present invention provides a method and a composition for maintaining the acidity level of a target composition within the range of +/−5% to +/−15%.

In one embodiment, the present invention provides a method and a composition for reducing the acidity level of a target composition by 2% to 80%. In another embodiment, the present invention provides a method and a composition for reducing the acidity level of a target composition by 2% to 15%. In one embodiment, the present invention provides a method and a composition for reducing the acidity level of a target composition by 5% to 20%. In one embodiment, the present invention provides a method and a composition for reducing the acidity level of a target composition by 10% to 30%. In one embodiment, the present invention provides a method and a composition for reducing the acidity level of a target composition by 20% to 60%.

In another embodiment, a composition as described herein prolongs the shelf-life and/or reduces and maintains the acidity of a target composition by inhibiting and/or reducing the oxidation rate of a target composition. In some embodiments, "a composition" is the novel composition of the invention as further described hereinbelow which reduces acidity, maintains acidity below a threshold level, and/or prolongs the shelf-life of the target composition. In some embodiments, "a target composition" is a composition to be treated with "a composition" as described herein. In some embodiments, "a target composition" is susceptible to oxidation during storage or manufacturing. In some embodiments, "a target composition" loses at least one benefit due to oxidation. In some embodiments, "a target composition" loses its value and/or its appearance due to oxidation. In some embodiments, "a target composition" is susceptible to color change due to oxidation or due to elevation in acidity.

In one embodiment, the present invention provides a composition comprising: a starch powder (such as flour), $SiO_2$ MgO, $Al_2O_3$, $Fe_2O_3$, and $K_2O$. In another embodiment, the present invention further provides that the composition is an edible composition. In another embodiment, the present invention further provides that the composition further comprises $3MgO.4SiO_2.H_2O$, $TiO_2$, MnO, $P_2O$ or any combination thereof. In another embodiment, the present invention further provides that the composition is mixed in oil such as plant oil. In another embodiment, the present invention further provides that a composition that is mixed in oil or was mixed in oil comprises a monoglyceride such as glycerol mono oleate. In another embodiment, the present invention further provides that any composition as described herein is devoid of an organic solvent.

In another embodiment, the present invention further provides a method for reducing the acidity, removing water, deodorizing, removing peroxides, or any combination thereof from plant oil, comprising the step of mixing a composition comprising: a starch powder (such as flour), $SiO_2$ MgO, $Al_2O_3$, $Fe_2O_3$, and $K_2O$ in the plant oil, thereby reducing the acidity, removing water, deodorizing, removing peroxides, or any combination thereof from plant oil. In another embodiment, the present invention further provides that reducing the acidity, removing water, deodorizing, removing peroxides, or any combination thereof from plant oil is extending the shelf life of the oil. In another embodiment, the present invention further provides that oil is olive oil and reducing the acidity is reducing the acidity to a value below 0.8% acidity.

In another embodiment, a composition a described herein is a topical and/or oral composition. In another embodiment, a composition a described herein is a therapeutic composition or a medicament. In another embodiment, a composition a described herein is an off-the-counter medication. In another embodiment, a composition a described herein is a nutraceutical.

In another embodiment, a composition a described herein is used for wound healing. In another embodiment, a composition a described herein is used for reducing and/or inhibiting inflammation. In another embodiment, a composition a described herein is used for reducing and/or inhibiting topical inflammation. In another embodiment, a composition a described herein is used for treating, reducing and/or inhibiting heartburn. In another embodiment, a composition a described herein is used for treating, reducing and/or inhibiting ulcer. In another embodiment, a composition a described herein is used for treating, reducing and/or inhibiting a peptic ulcer. In another embodiment, a composition a described herein is used for treating, reducing and/or inhibiting chronic gastro-esophageal severe heartburn. In another embodiment, a composition a described herein is used for treating, reducing and/or inhibiting gastro-esophageal reflux disease. In another embodiment, a composition a described herein is used for treating, reducing and/or inhibiting severe heartburn and/or gastrointestinal cysts. In another embodiment, a composition a described herein is used for treating, reducing and/or inhibiting gastrointestinal reflux disease (GERD). In another embodiment, a composition a described herein is used for treating, reducing and/or inhibiting acid reflux disease. In another embodiment, a composition a described herein reduces the symptoms of the above mentioned diseases and pathologies.

In another embodiment, treating is treating a subject. In another embodiment, a subject is a mammal. In another embodiment, a subject is a pet. In another embodiment, a subject is a farm animal. In another embodiment, a subject is a human subject.

In another embodiment, a composition as described herein further comprises pharmaceutically acceptable excipients, binders, diluents, preservatives or any combination thereof. In another embodiment, a composition as described herein further comprises pharmaceutically acceptable excipients suitable to the dosage form and the mode of administration (such as oral versus topical).

In another embodiment, the process and the composition of the invention for removing free fatty acids from oil do not create toxic molecules. In another embodiment, the process and the composition of the invention for removing free fatty acids from oil do not create trans-fatty acid structures. In another embodiment, the process and the composition of the invention further removes oxidized fatty acids. In another embodiment, the process and the composition of the invention further removes peroxides and free fatty acids. In another embodiment, the process and the composition of the invention further inhibits the production of peroxides and free fatty acids. In another embodiment, the process and the composition of the invention further remove pesticides and deodorizes the oil.

In another embodiment, the process and the composition of the invention further inhibits oxidation of oil. In another embodiment, the process and the composition of the invention further reduces the acidity of oil. In another embodiment, the process and the composition of the invention further reduces the acidity of oil to below 1.5%. In another embodiment, the process and the composition of the invention further reduces the acidity of oil to below 1.2%. In another embodiment, the process and the composition of the invention further reduces the acidity of oil to below 1.0%. In another embodiment, the process and the composition of the invention further reduces the acidity of oil to below 0.8%. In another embodiment, the process and the composition of the invention further reduces the acidity of oil to below 0.7%. In another embodiment, the process and the composition of the invention further reduces the acidity of oil to below 0.6%. In another embodiment, the process and the composition of the invention further reduces the acidity of oil to below 0.5%. In another embodiment, the process and the composition of the invention further reduces the acidity of oil to below 0.4% or 0.1%.

In another embodiment, acidity of oil correlated with the concentration of linolenic acid, and within the standards of the IOC for Virgin Olive Oils and within the standards of all kind of cold press oils.

In another embodiment, the process and the composition of the invention further reduces the peroxide value of oil. In another embodiment, the process and the composition of the invention further reduces the peroxide value of oil to less than 20 meq/kg. In another embodiment, the process and the composition of the invention further reduces the peroxide value of oil to a value of less than 15 meq/kg. In another embodiment, the process and the composition of the invention further reduces the peroxide value of oil to less than 12 meq/kg. In another embodiment, the process and the composition of the invention further reduces the peroxide value of oil to a value of less than 10 meq/kg. In another embodiment, the process and the composition of the invention further reduces the peroxide value of oil to less than 8 meq/kg. In another embodiment, the process and the composition of the invention further reduces the peroxide value of oil to a value of less than 5 meq/kg.

In another embodiment, the process and the composition of the invention further absorbs odors from oil. In another embodiment, the process and the composition of the invention further absorbs peroxides from oil. In another embodiment, the process and the composition of the invention has no negative impact on the environment.

In one embodiment, the composition of the invention comprises a combination of groups (a), (b), and (c), wherein (a) is flour, (b) is silicate, $SiO_2$, or their combination; and (c) is MgO, $Al_2O_3$, $Fe_2O_3$, $K_2O$, clay, wheat-germ or any combination thereof. In one embodiment, the composition of the invention comprises a combination of groups (a), (b), and (c), wherein (a) is flour, (b) is silicate, $SiO_2$, or their combination; and (c) is MgO, $Al_2O_3$, $Fe_2O_3$, $K_2O$, or any combination thereof. In one embodiment, the composition of the invention comprises a combination of groups (a), (b), and (c), wherein (a) is flour, (b) is silicate, $SiO_2$, or their combination; and (c) is clay, wheat-germ or their combination.

In one embodiment, the composition of the invention comprises: starch powder, $SiO_2$, MgO, $Al_2O_3$, $Fe_2O_3$ and $K_2O$. In another embodiment, starch powder is flour. In another embodiment, flour is white flour. In another embodiment, a composition as described herein further comprises $3MgO.4SiO_2.H_2O$. In another embodiment, a composition as described herein further comprises $TiO_2$. In another embodiment, a composition as described herein further comprises MnO. In another embodiment, a composition as described herein further comprises $P_2O$. In another embodiment, a composition as described herein further comprises Talc, $3MgO.4SiO_2.H_2O$, $TiO_2$, MnO, $P_2O$, or any combination thereof. In another embodiment, a composition as described herein further comprises vitamin E, polyphenols, other vitamins, sterols, or any combination thereof.

In another embodiment, a composition as described herein comprises a starch source (such as flour), clay, wheat-germ, and silicate. In another embodiment, silicate is $3MgO.4SiO_2.H_2O$. In another embodiment, a composition as described herein comprises a starch source (such as flour), clay, wheat-germ, oil and silicate. In another embodiment, a composition as described herein comprises a starch source (such as flour), clay, wheat-germ, oil, glycerol mono-oleate and silicate.

In another embodiment, a composition as described herein comprises 0.5 to 50% (w/w) by weight wheat-germ. In another embodiment, a composition as described herein comprises 1 to 30% (w/w) by weight wheat-germ. In another embodiment, a composition as described herein comprises 2 to 20% (w/w) by weight wheat-germ. In another embodiment, a composition as described herein comprises 4 to 15% (w/w) by weight wheat-germ. In another embodiment, a composition as described herein comprises 8 to 12% (w/w) by weight wheat-germ.

In another embodiment, a composition as described herein comprises 0.5 to 70% (w/w) by weight a starch source (such as flour). In another embodiment, a composition as described herein comprises 1 to 50% (w/w) by weight a starch source (such as flour). In another embodiment, a composition as described herein comprises 4 to 50% (w/w) by weight a starch source (such as flour). In another embodiment, a composition as described herein comprises 2 to 15% (w/w) by weight a starch source (such as flour). In another embodiment, a composition as described herein comprises 10 to 30% (w/w) by weight a starch source (such as flour). In another embodiment, a composition as described herein comprises 10 to 50% (w/w) by weight a starch source (such as flour). In another embodiment, a composition as described herein comprises 20 to 50% (w/w) by weight a starch source (such as flour). In another embodiment, a composition as described herein comprises 20 to 40% (w/w) by weight a starch source (such as flour).

In another embodiment, a composition as described herein comprises 5 to 80% (w/w) by weight clay. In another embodiment, a composition as described herein comprises 5 to 20% (w/w) by weight clay. In another embodiment, a composition as described herein comprises 10 to 70% (w/w) by weight clay. In another embodiment, a composition as described herein comprises 15 to 60% (w/w) by weight clay. In another embodiment, a composition as described herein comprises 20 to 60% (w/w) by weight clay. In another embodiment, a composition as described herein comprises 30 to 50% (w/w) by weight clay. In another embodiment, a composition as described herein comprises 35 to 45% (w/w) by weight clay.

In another embodiment, a composition as described herein comprises 5 to 60% (w/w) by weight silicate. In another embodiment, a composition as described herein comprises 10 to 50% (w/w) by weight silicate. In another embodiment, a composition as described herein comprises 5 to 15% (w/w) by weight silicate. In another embodiment, a composition as described herein comprises 15 to 45% (w/w) by weight silicate. In another embodiment, a composition as described herein comprises 20 to 40% (w/w) by weight silicate. In another embodiment, a composition as described herein comprises 25 to 35% (w/w) by weight silicate.

In another embodiment, a composition as described herein comprises at least 55% (w/w) by weight oil. In another embodiment, a composition as described herein comprises at least 65% (w/w) by weight oil. In another embodiment, a composition as described herein comprises at least 75% (w/w) by weight oil. In another embodiment, a composition as described herein comprises at least 80% (w/w) by weight oil. In another embodiment, a composition as described herein comprises at least 85% (w/w) by weight oil. In another embodiment, a composition as described herein comprises at least 90% (w/w) by weight oil. In another embodiment, a composition as described herein comprises at least 95% (w/w) by weight oil. In another embodiment, a composition as described herein comprises from 0.2 to 5 kg of a dry composition per 1 ton of pretreated oil. In another embodiment, a composition as described herein comprises from 0.2 to 2 kg of a dry composition per 1 ton of pretreated oil. In another embodiment, a composition as described herein comprises from 0.5 to 2 kg of a dry composition per 1 ton of pretreated oil. In another embodiment, a composition as described herein comprises from 0.7 to 1.3 kg of a dry composition per 1 ton of pretreated oil. In another embodiment, a composition as described herein comprises about 1 kg of a dry composition per 1 ton of pretreated oil.

In another embodiment, a composition as described herein is devoid of a solvent. In another embodiment, a composition as described herein is devoid of an organic solvent. In another embodiment, a composition as described herein comprises wheat germ, flour, and clay.

In another embodiment, the composition of the invention further comprises fruit or vegetable pulp. In another embodiment, the composition of the invention further comprises crushed fruit or vegetable. In another embodiment, the composition of the invention further comprises grind fruit or vegetable.

In another embodiment, Clay comprises 40-60% (w/w) by weight $SiO_2$. In another embodiment, Clay comprises 50-60% (w/w) by weight $SiO_2$. In another embodiment, Clay comprises 52-56% (w/w) by weight $SiO_2$.

In another embodiment, Clay comprises 20-50% (w/w) by weight MgO. In another embodiment, Clay comprises 20-40% (w/w) by weight MgO. In another embodiment, Clay comprises 28-32% (w/w) by weight MgO.

In another embodiment, Clay comprises 2-8% (w/w) by weight $Al_2O_3$. In another embodiment, Clay comprises 3-6% (w/w) by weight $Al_2O_3$. In another embodiment, Clay comprises 3-5% (w/w) by weight $Al_2O_3$. In another embodiment, Clay comprises 3.5-4.5% (w/w) by weight $Al_2O_3$.

In another embodiment, Clay comprises 0.2-5% (w/w) by weight $Fe_2O_3$. In another embodiment, Clay comprises 0.2-2% (w/w) by weight $Fe_2O_3$. In another embodiment, Clay comprises 0.5-3% (w/w) by weight $Fe_2O_3$. In another embodiment, Clay comprises 1-2% (w/w) by weight $Fe_2O_3$.

In another embodiment, Clay comprises 0.1-5% (w/w) by weight $K_2O$. In another embodiment, Clay comprises 0.3-3% (w/w) by weight $K_2O$. In another embodiment, Clay comprises 0.5-2% (w/w) by weight $K_2O$. In another embodiment, Clay comprises 0.8-1.2% (w/w) by weight $K_2O$.

In another embodiment, Clay comprises 1-20% (w/w) by weight LO1. In another embodiment, Clay comprises 5-15% (w/w) by weight LO1. In another embodiment, Clay comprises 8-12% (w/w) by weight LO1. In another embodiment, Clay comprises 7-10% (w/w) by weight LO1.

In another embodiment, a composition as described herein comprises 10-70% (w/w) by weight $SiO_2$. In another embodiment, a composition as described herein comprises 20-70% (w/w) by weight $SiO_2$ In another embodiment, a composition as described herein comprises 30-60% (w/w) by weight $SiO_2$ In another embodiment, a composition as described herein comprises 40-50% (w/w) by weight $SiO_2$ In another embodiment, a composition as described herein comprises 10-70% (w/w) by weight MgO. In another embodiment, a composition as described herein comprises 10-50% (w/w) by weight MgO. In another embodiment, a composition as described herein comprises 20-40% (w/w) by weight MgO. In another embodiment, a composition as described herein comprises 25-35% (w/w) by weight MgO.

In another embodiment, a composition as described herein comprises 10-15% (w/w) by weight $Al_2O_3$. In another embodiment, a composition as described herein comprises 3-15% (w/w) by weight $Al_2O_3$. In another embodiment, a composition as described herein comprises 7-12% (w/w) by weight $Al_2O_3$. In another embodiment, a composition as described herein comprises 8-10% (w/w) by weight $Al_2O_3$.

In another embodiment, clay comprises: 62-72% (w/w) by weight $SiO_2$, 0.2-0.8% w/w) by weight $TiO_2$, 10-15% (w/w) by weight $Al_2O_3$, 2-8% (w/w) by weight $Fe_2O_3$, 0.01-0.5% (w/w) by weight MnO, 2-8% (w/w) by weight MgO, 0.5-5% (w/w) by weight wheat germ, 0.5-3% (w/w) by weight $K_2O$, and 0.5-5% (w/w) by weight $P_2O_3$.

In another embodiment, a dry composition as described herein comprises 10-40% (w/w) flour. In another embodiment, a dry composition as described herein comprises 15-30% (w/w) flour. In another embodiment, a dry composition as described herein comprises 20-30% (w/w) flour. In another embodiment, a dry composition as described herein comprises 25-27% (w/w) flour.

In another embodiment, a dry composition as described herein comprises 1-20% (w/w) wheat germ. In another embodiment, a dry composition as described herein comprises 1-10% (w/w) wheat germ. In another embodiment, a dry composition as described herein comprises 2-9% (w/w) wheat germ. In another embodiment, a dry composition as described herein comprises 6-8% (w/w) wheat germ.

In another embodiment, a dry composition as described herein comprises 2-20% wheat germ, 15-40% flour, 8-30% clay, and 18-40% lamellar talc. In another embodiment, a dry composition as described herein comprises 5-15% wheat germ, 20-30% flour, 12-25% clay, and 25-35% lamellar talc. In another embodiment, a dry composition as described herein comprises 6-8% wheat germ, 24-28% flour, 16-24% clay, and 25-32% lamellar talc.

In another embodiment, a composition as described herein further comprises oil. In another embodiment, a composition as described herein comprising oil further comprises monoglyceride. In another embodiment, a composition as described herein comprising oil further comprises mono-oleate.

In another embodiment, oil is any neutral, nonpolar chemical substance that is a viscous liquid at ambient temperatures, and is immiscible with water but soluble in alcohols or ethers. In another embodiment, oil is organic oil. In another embodiment, oil is plant oil. In another embodiment, oil is produced by cold press. In another embodiment, oil comprises steroids, proteins, waxes, alkaloids, or any combination thereof.

In another embodiment, oil is crude oil. In another embodiment, oil is an edible oil. In another embodiment, oil is a lubricant or used as fuel. In another embodiment, oil is sunflower oil. In another embodiment, oil is coconut oil. In another embodiment, oil is corn oil. In another embodiment, oil is cottonseed oil. In another embodiment, oil is olive oil. In another embodiment, oil is palm oil. In another embodiment, oil is peanut oil. In another embodiment, oil is rapeseed oil, including Canola oil. In another embodiment, oil is safflower oil. In another embodiment, oil is sesame oil. In another embodiment, oil is soybean oil. In another embodiment, oil is hazelnut oil. In another embodiment, oil is nut oil. In another embodiment, oil is almond oil. In another embodiment, oil is beech nut oil. In another embodiment, oil is cashew oil. In another embodiment, oil is macadamia oil.

In another embodiment, oil is mongongo nut oil. In another embodiment, oil is pine nut oil. In another embodiment, oil is pistachio oil. In another embodiment, oil is walnut oil. In another embodiment, oil is citrus oil. In another embodiment, oil is an oil from melon or gourd seeds. In another embodiment, oil is borage seed oil. In another embodiment, oil is blackcurrant oil. In another embodiment, oil is evening primrose oil. In another embodiment, oil comprises more than 5% gamma-Linolenic acid (GLA). In another embodiment, oil is açai oil. In another embodiment, oil is black seed oil. In another embodiment, oil is flaxseed oil. In another embodiment, oil is carob pod oil. In another embodiment, oil is amaranth oil. In another embodiment, oil is apricot oil. In another embodiment, oil is apple seed oil. In another embodiment, oil is argan oil. In another embodiment, oil is avocado oil. In another embodiment, oil is babassu oil. In another embodiment, oil is ben oil. In another embodiment, oil is borneo tallow nut oil. In another embodiment, oil is cape chestnut oil. In another embodiment, oil is cocoa butter oil. In another embodiment, oil is cocklebur oil. In another embodiment, oil is cohune oil. In another embodiment, oil is coriander seed oil. In another embodiment, oil is date seed oil. In another embodiment, oil is dika oil. In another embodiment, oil is false flax oil. In another embodiment, oil is made of the seeds of *Camelina sativa*. In another embodiment, oil is grape seed oil. In another embodiment, oil is hemp oil. In another embodiment, oil is kapok seed oil. In another embodiment, oil is kenaf seed oil. In another embodiment, oil is lallemantia oil.

In another embodiment, oil is mafura oil. In another embodiment, oil is marula oil. In another embodiment, oil is meadowfoam seed oil. In another embodiment, oil is mustard oil. In another embodiment, oil is poppyseed oil. In another embodiment, oil is okra seed oil. In another embodiment, oil is *papaya* seed oil. In another embodiment, oil is *perilla* seed oil. In another embodiment, oil is persimmon seed oil. In another embodiment, oil is pequi oil In another embodiment, oil is pili nut oil. In another embodiment, oil is pomegranate seed oil. In another embodiment, oil is prune kernel oil. In another embodiment, oil is *quinoa* oil.

In another embodiment, oil is ramtil oil. In another embodiment, oil is rice bran oil. In another embodiment, oil is royle oil. In another embodiment, oil is sacha inchi oil. In another embodiment, oil is sapote oil. In another embodiment, oil is seje oil. In another embodiment, oil is taramira oil. In another embodiment, oil is Tea seed oil. In another embodiment, oil is thistle oil. In another embodiment, oil is tigernut oil. In another embodiment, oil is tobacco seed oil. In another embodiment, oil is tomato seed oil. In another embodiment, oil is wheat germ oil. In another embodiment, oil is any combination of two or more oils disclosed herein.

In another embodiment, oil to be used by the process of the invention or oil comprising a composition as described herein is extracted from a plant such as but not limited to olives and/or olive pulps.

In another embodiment, the term "oil" is oil to be used by the process of the invention. In another embodiment, the term "oil" is oil comprising a composition as described herein.

Process

In another embodiment, oil is extracted from cleaned/washed olives where the stems, leaves, twigs, and other debris left with the olives are removed. In another embodiment, the composition of the invention is added to the fruit or the vegetable which is the source of oil (such as adding the composition to crushed olives and/or vegetable or fruit pulp). oil is manufactured by crushing the olives into a paste. In another embodiment, crushing the olives is done with stone mills, metal tooth grinders, or various kinds of hammermills. In another embodiment, the paste undergoes a malaxing (mixing) process (5-240 minutes) which allows the formation of oil droplets. In another embodiment, the paste is then heated. In another embodiment, water is added to the paste. In another embodiment, the paste mixer is a horizontal trough with spiral mixing blades. In another embodiment, the next step comprises separating the oil from the rest of the olive components. In another embodiment, this is done with presses. In another embodiment, this is done by centrifugation. In another embodiment, centrifugation is three-phase centrifugation which separates the oil from water and solids. In another embodiment, centrifugation is two-phase centrifugation which separates the oil from a wet paste. In another embodiment, oil is then left in tanks or barrels where a final separation, if needed, happens through gravity—racking the oil. In another embodiment, oil is further filtered In another embodiment, the present invention is directed to a method for obtaining refined Olive Oil by treating an oil having acidity exceeding 0.8% with the composition described herein and according to the methods described herein.

In another embodiment, the present invention is directed to a method for obtaining refined Olive Oil from virgin olive oils without any alterations of the glyceridic structure of the oil, without the use of solvents and without heating the oil. In another embodiment, a process as described herein is free of any change in the existing production process in the oil during the cold press process in the oil mill. In another embodiment, a process as described herein involves removal of acidity in cold press oils such as but not limited to olive oil. In another embodiment, olive oil is a virgin olive oil (Section 2.1.1 of the International Olive Oil Council (IOOC). In another embodiment, olive oil is an extra virgin olive oil (Section 2.1.1 (i) of the International Olive Oil Council (IOOC). In another embodiment, a process as described herein takes place at room temperature using physical treatment only by which it eliminates all of the undesired acidic molecules, without causing any adverse changes to the chemical composition of the oil, and without the use of any aggressive organic solvents.

In another embodiment, a process as described herein amounts to adding a mixture of various absorbing substances to the oil during the cold press process in the oil mill through the process which is full accordance with the CODEX. In another embodiment, a process as described herein includes substances that are all environmentally friendly, and have been approved as food grades for the oils industry without any hazardous effect on human beings. In another embodiment, a process as described herein is with credence of the CODEX limitations of being "process of mixing" and process of "Separating and centrifuging". Environmentally friendly substances, according to some embodiments, quickly separate from the olive oil after accreting all of the unwanted molecules, leaving no residue in the olive oil itself. In another embodiment, a process as described herein includes a centrifugation step wherein the oil, to be produced as an Extra virgin with an acidity of less than 0.1%. In another embodiment, oil, is treated by adding the composition of the invention to the source (vegetable or fruits from which the oil is extracted from) and before the "process of mixing", without any changes in the regular cold press process. In another embodiment, a process as described includes cold press olive oil, treated by composition of the invention which reduces the acidity of the oil followed by filtration and is defined as virgin olive oils, according to the International Olive Oil Council.

In another embodiment, the present invention is directed to a method for reducing the acidity of cold press edible oils to values that meets standards and regulations of each kind of oil. In another embodiment, the method does not remove antioxidants from oil. In another embodiment, the present invention is directed to a method for drying oil and extending its shelf life. In another embodiment, the method is free of a cis-trans transformation. In another embodiment, the present method further deodorizes the oil. In another embodiment, the present invention is directed to a method for the treatment and improvement of cold-pressed edible oils (such as adding the composition of the invention to the fruit or vegetable (in the form of pulp/crushed etc.) which serve as the source oil) in the oil mill. In another embodiment, the method of the invention is performed during the manufacturing process of edible oils as described herein. In another embodiment, the method of the invention is performed during the manufacturing process of extra virgin oil.

In another embodiment, the present invention is directed to a method for reducing the acidity in cold press olive oils to values that meets standards and regulations. In another embodiment, the method does not remove antioxidants from olive oil. In another embodiment, the present invention is directed to a method for drying oil and extending its shelf life. In another embodiment, the method is free of a cis-trans transformation. In another embodiment, the present method further deodorizes the olive oil. In another embodiment, the present invention is directed to a method for the treatment and improvement of cold-pressed olive oils in particular. In another embodiment, the method of the invention is performed during the manufacturing process of olive oils as described herein. In another embodiment, the method of the invention is performed during the manufacturing process of extra virgin olive oil.

In another embodiment, oil treated with the composition of the present invention has specific gravity of 0.9120-0.9190 at 15.5° C. In another embodiment, oil treated with the composition of the present invention has viscosity of 82-85 mPa·s (84 cP) at 20° C. In another embodiment, oil treated with the composition of the present invention has Specific Heat of 1-3 J/(g.)(° C.) at 82-85 (° F.). In another embodiment, oil treated with the composition of the present invention has thermal conductivity of 0.15-0.2 at 20° C. In another embodiment, oil treated with the composition of the present invention has Dielectric Constant, e of 2.7-3.4 at 20° C. In another embodiment, oil treated with the composition of the present invention has density of 900-940 kg/m3 at 20° C. In another embodiment, oil treated with the composition of the present invention has Volumetric Heat Capacity of 1.6-1.7 106 J/m3 at 20° C. In another embodiment, oil treated with the composition of the present invention has Thermal Diffusivity of $10 \times 10^{-8}$ m$^2$/s at 20° C. In another embodiment, oil treated with the composition of the present invention has a boiling point at 530-600 degrees Fahrenheit. In another embodiment, oil treated with the composition of the present invention has about 120 calories per Tablespoon.

In another embodiment, the manufacturing process of oil depends entirely on mechanical means without the use of any solvents. In another embodiment, the manufacturing process of oil is performed in of less than 86° F., 30° C.

In another embodiment, oil undergone the treatment according to the method of the invention is enriched with phenolic compounds which contribute to the stability of the oil, antioxidant properties, lipoxygenase activity inhibition and microbial activity. In another embodiment, phenolic compounds include but are not limited to oleuropein aglycone. In another embodiment, oil undergone the treatment according to the method of the invention is enriched with beta-carotene. In another embodiment, oil undergone the treatment according to the method of the invention is enriched with lutein and/or zeaxanthin.

In another embodiment, a composition of the invention absorbs of water within oil. In another embodiment, the method and composition of the invention reduces the amount of water within oil. In another embodiment, the method and composition of the invention reduces the amount of free glycerol and free fatty acids in oil. In another embodiment, the method of the invention enhances the quality of virgin olive oils or other plant oils. In another embodiment, the method of the invention utilizes virgin olive oils or other plant oils as starting material. In another embodiment, "enhances the quality" is reducing the acidity, reducing water content, reducing the amount of peroxides, enhancing the appearance (turbidity etc.), limiting unpleasant odors, increasing favorable odors (hexanal), increasing taste or any combination thereof.

In another embodiment, "enhances the quality" is enhancing the oil's aroma and/or taste for: green apple, almond: nutty (fresh not oxidized) artichoke, astringent, banana, bitter/buttery, *eucalyptus*, floral, forest, fresh, fruity, green tea, harmonious, hay/straw, green/greenly, grass, herbaceous, melon, mint, pear, peach, peppery, pungent, ripely, round, spice, sweet, tomato, tropical, walnut, wheatgrass, woody, or any combination thereof. In another embodiment, "enhances the quality" is reducing the oil's aroma and/or taste for: acetone, blue cheese, brine, bacon, burnt/heated, cucumber, dirty, waste water, dreggish, esparto, fiscolo, flat/bland, frozen/wet, wood, fusty, greasy, grubby, barnyard-like aroma, musty, moldy, metallic, rancid, greasy, sour milk, stale nuts, unbalanced, winey, vinegary, yeasty, or any combination thereof.

This invention is illustrated in the Experimental Details section which follows. These sections are set forth to aid in an understanding of the invention but are not intended to, and should not be construed to limit in any way the invention as set forth in the claims which follow thereafter.

As used herein, the singular forms "a", "an", and "the" include plural forms unless the context clearly dictates otherwise. Thus, for example, reference to "a therapeutic agent" includes reference to more than one therapeutic agent.

Unless specifically stated or obvious from context, as used herein, the term "or" is understood to be inclusive.

The term "including" is used herein to mean, and is used interchangeably with, the phrase "including but not limited to".

As used herein, the terms "comprises," "comprising," "containing," "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments. In another embodiment, the term "comprise" includes the term "consist".

In another embodiment, any recitation of "%" is weight/weight %, volume/volume % or weight/volume %.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Example 1: Sampling and Evaluation of Oil Quality Before and after Treatment

The experimental section provides chemical and physical evaluation of virgin oils as well as other oils including Canola, sesame, grape seed and flax oils from cold press process before applying and after applying the methods and composition of the invention.

Samples

Oil samples were obtained from simple cold pressing and were transferred to sealed glass containers and were kept in cool conditions. The samples were further examined in an oil analytical lab.

A portion from the same cold press treatment (same batch and same sample) was treated with the compositions of the invention including physical purification procedure treating formula (treated samples). Once the process was completed the treated samples were similarly transferred to sealed glass containers, marked, kept in cool conditions and transferred to the analytical lab for testing.

Composition

The composition that was applied to the oil (treated group) included (all in weight percent): wheat germ (7%), flour (26%), Clay with a complex of oxides (20% total) the oxides: Na (30%). K (42.6%). AL (27.4%), clay comprising complex of hormite and smechite minerals (15%), clay comprising $SiO_2$, $MgO$, $Al_2O_3$, $Fe_2O_3$, $K_2O$, LO1 (4%), and complex of $SiO_2$, $MgO$, $Al_2O_3$ (28%).

Process

Oil containers are treated with the composition as described above. Between 0.4 to 3 Kg of the composition was applied to 1 ton of pretreated oil. After about an hour the oil comprising the composition is filtered thus substantially removing the previously added composition.

Tests

The following tests were performed: Fatty acids profile; Free fatty acids (FFA, acidity); Refractive index; Unsaponifiables matter; Moisture content, UV (at 270 nm) absorption, Iodine Value and Peroxide Value.

In addition all the samples were examined for their appearance, clarity, transparency and taste by the expert.

The most relevant results are those examining the acidity of the virgin oils as well as the acidity of several other oils that were selected at random.

Tables 1 and 2 provide analytical results of treated and untreated cold press oil:

TABLE 1 untreated oil
Analysis Results

| Test | Units | Range | Results |
|---|---|---|---|
| Palmitic acid (C16:0) | gr/100 gr fat | | 5.23 |
| Stearic acid (C18:0) | gr/100 gr fat | | 3.31 |
| Oleic acid (C18:1) | gr/100 gr fat | | 20.18 |
| Linoleic acid (C18:2) | gr/100 gr fat | | 15.74 |
| Linolenic acid (C18:3) | gr/100 gr fat | | 55.53 |
| Free fatty acid (FFA) | %(oleic acid) | | 4.7 |
| Refrective index | — | | 1.481 |
| Unsaponifiable matter | % | | 1.0 |
| Uv- Absorption | — | | 0.3 |
| Iodine value | mg I2/gr oil | 170-204 | 186.8 |

TABLE 2 treated oil
Analysis Results

| Test | Units | Range | Results |
|---|---|---|---|
| Palmitic acid (C16:0) | gr/100 gr fat | 5-6 | 5.25 |
| Stearic acid (C18:0) | gr/100 gr fat | 3-5 | 3.27 |
| Oleic acid (C18:1) | gr/100 gr fat | 18-26 | 17.26 |

TABLE 2-continued treated oil
Analysis Results

| Test | Units | Range | Results |
|---|---|---|---|
| Linoleic acid (C18:2) | gr/100 gr fat | 14-20 | 15.83 |
| Linolenic acid (C18:3) | gr/100 gr fat | 51-56 | 58.39 |
| Free fatty acid (FFA) | %(oleic acid) | | 0.1 |
| Refrective index | — | | 1.482 |
| Unsaponifiable matter | % | | 0.9 |
| Uv- Absorption | — | | 0.2 |
| Iodine value | mg I2/gr oil | 170-204 | 190.0 |

(1) The acidity of all the tested samples was 0.1% or less (measured as oleic acid). The most relevant tests are of virgin oils that the acidity was reduced from 3.2 and 4.8 before the treatment to 0.07 and 0.2, respectively, after the treatment (the reduction in the acidity to 0.07 is 10 fold lower than expected or measured for extra virgin olive oil). The acidity of the remaining oils was dramatically improved in the treated oil compared to the untreated oil and all the values were less than those required for extra virgin oils; i.e. 0.1% (as oleic acid).

2) Fatty acids Profile—fatty acids profiles including the saturated stearic and palmitic contents were kept unchanged. The unsaturated and polyunsaturated fatty acids also remained at their original content.

3) The linolenic acid content—met the health recommendations and the international standards.

4) UV absorption—Untreated samples had values that exceeded the range required for extra virgin oil. All treated samples had UV absorbance values within the range required by the regulations for extra virgin oil (olive oil standards of the International Olive Council (IOC)).

5) The unsaponifiable matter—was below the allowed standard (value of 0.9% of the treated sample vs. 1.5 for the untreated sample (as per the regulation standards).

6) The moisture content—was reduced significantly (at least 4 folds reduction) in the treated sample to 0.076% (0.076 gram/100 gram). This extremely low value indicated that there is no water (moisture) that can promote acidity during storage of the oil.

7) The iodine value (IV)—did not change due to the treatment and was exactly within the permitted scale of values (IV of 83.5 for treated samples oil vs. 80-88 mg iodine per gram of oil. This was a good indication regarding the authenticity of the olive oil.

8) Pesticides—The results showed small amount of pesticides in the untreated oil wherein the treated oil was pesticides free (not detected—ND, see Certificate of Analysis).

These results are unexpected for oils that undergone cold press extract and not a harmful refining process.

These results clearly indicate that the present method and composition are extremely effective in upgrading cold press oils with high acidity into highly pure oils of high quality. This means that oils of low grade can be upgraded to without altering physical properties.

CONCLUSIONS

The method utilizing the composition of the invention was utilized in the production of high quality plant oils from cold extraction after treating the crude oil with the new composition.

The method utilizing the composition of the invention drastically reduces the acidity of oils without heating and using solvents.

The nutritionally valuable compounds within the oil remain unaltered.

The oils resulting from the methods of the invention are very dry thus guaranteeing extended shelf life.

This novel technology is suitable for any plant oil.

What is claimed is:

1. A method for reducing the acidity, removing water, deodorizing, removing peroxides, or any combination thereof from plant oil, comprising the step of mixing a composition comprising: flour, $SiO_2$, MgO, $Al_2O_3$, $Fe_2O_3$, and $K_2O$ in said plant oil, wherein the step of mixing is performed at a temperature of less than 30°; thereby reducing the acidity, removing water, deodorizing, removing peroxides, or any combination thereof from plant oil.

2. The method of claim 1, wherein said oil is olive oil and said reducing the acidity is reducing the acidity to a value below 0.8% acidity.

* * * * *